(12) United States Patent
Rezach et al.

(10) Patent No.: US 9,962,171 B2
(45) Date of Patent: May 8, 2018

(54) SURGICAL INSTRUMENT AND METHOD

(71) Applicant: Warsaw Orthopedic, Inc., Warsaw, IN (US)

(72) Inventors: William Alan Rezach, Atoka, TN (US); Christopher M. Patterson, Olive Branch, MS (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 0 days. days.

(21) Appl. No.: 14/734,849

(22) Filed: Jun. 9, 2015

(65) Prior Publication Data
US 2016/0361074 A1    Dec. 15, 2016

(51) Int. Cl.
*A61B 17/70* (2006.01)
*A61B 17/17* (2006.01)
*A61B 17/02* (2006.01)

(52) U.S. Cl.
CPC ...... *A61B 17/1757* (2013.01); *A61B 17/7071* (2013.01); *A61B 2017/0256* (2013.01)

(58) Field of Classification Search
CPC ............ A61B 17/1757; A61B 17/7071; A61B 2017/0256
See application file for complete search history.

(56) References Cited

U.S. PATENT DOCUMENTS

| | | | | |
|---|---|---|---|---|
| 4,907,577 A * | 3/1990 | Wu | ..................... | A61B 17/1757 606/104 |
| 6,342,056 B1 * | 1/2002 | Mac-Thiong | ...... | A61B 17/1757 606/103 |
| 7,455,685 B2 * | 11/2008 | Justis | ................. | A61B 17/1757 606/246 |
| 7,909,878 B2 * | 3/2011 | Blatt | .................. | A61B 17/1757 606/86 A |
| 7,959,677 B2 * | 6/2011 | Landry | ............. | A61B 17/1757 623/17.11 |
| 7,976,569 B2 * | 7/2011 | Justis | ................. | A61B 17/1757 606/279 |
| 8,419,739 B2 * | 4/2013 | Jamali | .................... | A61B 17/15 606/246 |
| 8,900,237 B2 * | 12/2014 | Ramsay | ............. | A61B 17/1735 606/104 |
| 9,149,286 B1 * | 10/2015 | Greenhalgh | ....... | A61B 17/1757 |
| 2006/0084986 A1 * | 4/2006 | Grinberg | .............. | A61B 17/025 606/86 A |
| 2006/0085010 A1 * | 4/2006 | Lieberman | ......... | A61B 17/1757 606/99 |
| 2007/0016296 A1 * | 1/2007 | Triplett | .............. | A61B 17/1757 623/17.11 |
| 2008/0009881 A1 * | 1/2008 | Blatt | .................. | A61B 17/1757 606/99 |
| 2008/0125814 A1 * | 5/2008 | Yuan | .................. | A61B 17/1757 606/247 |
| 2008/0161810 A1 * | 7/2008 | Melkent | ............. | A61B 17/1659 606/79 |
| 2010/0023018 A1 * | 1/2010 | Theofilos | ........... | A61B 17/1757 606/96 |

(Continued)

*Primary Examiner* — Jacqueline Johanas

(57) ABSTRACT

A surgical instrument comprises a first member connected with tissue. A second member is connected with the first member and configured to orient at least one surgical tool along at least one selected path for penetrating tissue. Systems and methods of use are disclosed.

18 Claims, 5 Drawing Sheets

(56) References Cited

U.S. PATENT DOCUMENTS

| | | | |
|---|---|---|---|
| 2010/0324560 A1* | 12/2010 | Suda | A61B 17/1757 606/79 |
| 2011/0009869 A1* | 1/2011 | Marino | A61B 17/1757 606/87 |
| 2011/0046628 A1* | 2/2011 | Jamali | A61B 17/15 606/87 |
| 2011/0245838 A1* | 10/2011 | Marino | A61B 17/1637 606/96 |
| 2012/0022599 A1* | 1/2012 | Ludwig | A61B 17/7088 606/279 |
| 2014/0200618 A1* | 7/2014 | Donner | A61B 17/1757 606/281 |
| 2014/0350614 A1* | 11/2014 | Frey | A61B 17/1757 606/86 R |
| 2015/0182268 A1* | 7/2015 | Donner | A61B 17/8066 606/281 |
| 2015/0335372 A1* | 11/2015 | Schifano | A61F 2/4611 623/17.16 |
| 2016/0030067 A1* | 2/2016 | Frey | A61B 17/1757 606/86 A |
| 2016/0302834 A1* | 10/2016 | Abdou | A61F 2/4455 |
| 2016/0338714 A1* | 11/2016 | Schoenefeld | A61B 17/1757 |
| 2016/0346015 A1* | 12/2016 | Triplett | A61B 17/1757 |

* cited by examiner

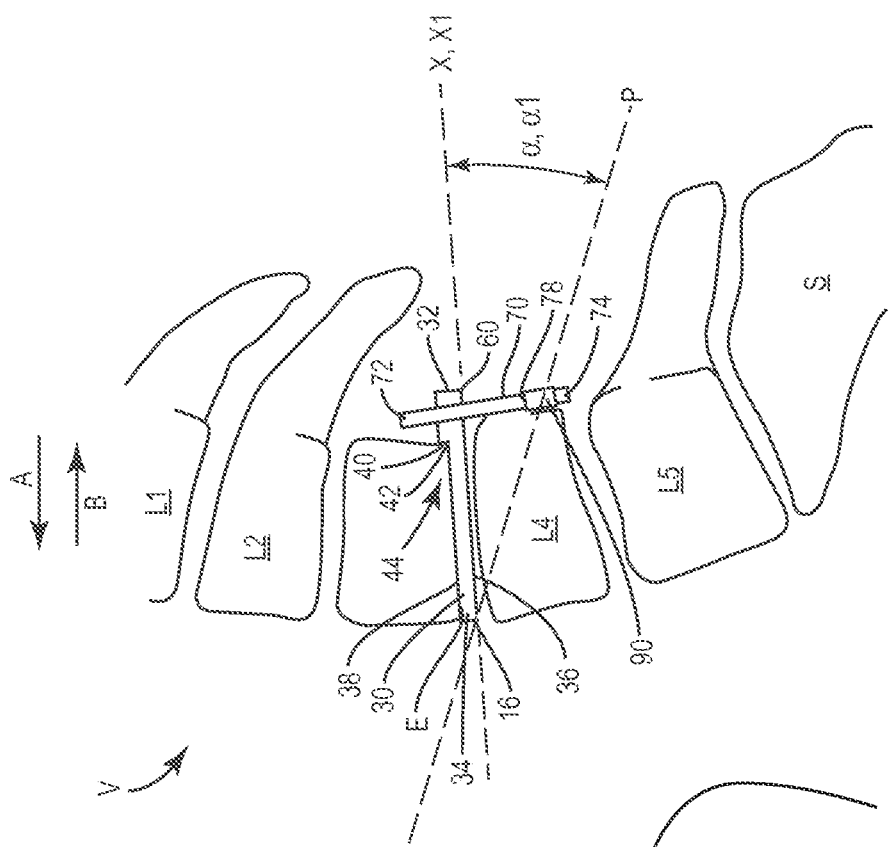

\# SURGICAL INSTRUMENT AND METHOD

TECHNICAL FIELD

The present disclosure generally relates to medical devices for the treatment of musculoskeletal disorders, and more particularly to a surgical system and a method for correction of a spine disorder.

BACKGROUND

Spinal pathologies and disorders such as scoliosis and other curvature abnormalities, kyphosis, degenerative disc disease, disc herniation, osteoporosis, spondylolisthesis, stenosis, tumor, and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, fusion, fixation, osteotomy, discectomy, laminectomy and implantable prosthetics. Vertebral tissue, for example, all or a portion of vertebrae, can be treated and/or removed as part of a correction treatment. These correction treatments may employ implants that are manipulated for engagement with vertebrae to position and align one or more vertebrae. This disclosure describes an improvement over these prior art technologies.

SUMMARY

In one embodiment, a surgical instrument is provided. The surgical instrument comprises a first member connected with tissue. A second member is connected with the first member and configured to orient at least one surgical tool along at least one selected path for penetrating tissue. In some embodiments, systems and methods are disclosed.

BRIEF DESCRIPTION OF THE DRAWINGS

The present disclosure will become more readily apparent from the specific description accompanied by the following drawings, in which:

FIG. 1 is a plan view of components of one embodiment of a system in accordance with the principles of the present disclosure disposed with vertebrae;

FIG. 2 is a plan view of the components of the system shown in FIG. 1 disposed with vertebrae;

DETAILED DESCRIPTION

Figure 3:
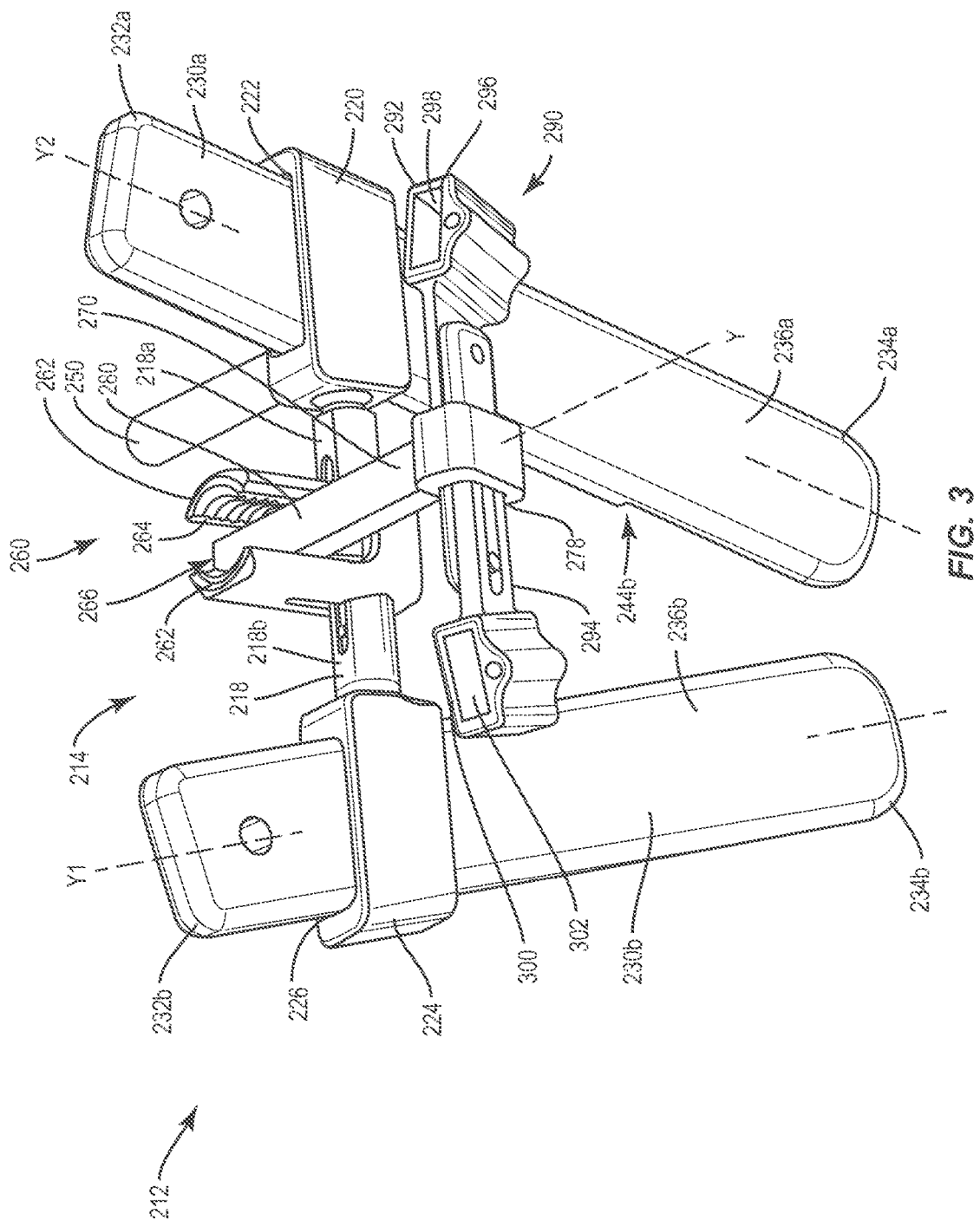
FIG. 3 is a perspective view of components of one embodiment of a system in accordance with the principles of the present disclosure.

The exemplary embodiments of a surgical system are discussed in terms of medical devices for the treatment of musculoskeletal disorders and more particularly, in terms of a surgical system and a method for correction of a spine disorder. In some embodiments, the present disclosure provides a surgical system including a surgical instrument that can be employed with a surgical procedure, such as, for example, a correction treatment to treat trauma of the spine, such as, for example, thoraco-lumbar and/or lumbar fractures. In some embodiments, the surgical instrument can be employed with a surgical procedure, such as, for example, a method for treating a patient with a pedicle subtraction osteotomy (PSO) or a vertebral column resection (VCR). In some embodiments, the surgical instrument can be employed with a method for correction of deformities such as kyphosis or scoliosis. In some embodiments, the surgical instrument can be employed with a posterior VCR to correct angular and fixed kyphotic deformity, such as post traumatic deformity, congenital deformity and/or post infectious deformity.

In some embodiments, the surgical system comprises a surgical instrument that orients a surgical tool along a selected path for penetrating tissue, such as, for example, cutting and/or removing all or a portion of vertebrae. In some embodiments, the surgical instrument includes a guide. In some embodiments, the surgical instrument includes a cutting jig that includes a guide. In some embodiments, the cutting jig can be employed with osteotomy procedures. In some embodiments, the surgical instrument is connected to at least one bone fastener fixed with tissue and includes a guide that orients a surgical tool along a selected path for penetrating tissue.

In some embodiments, the surgical instrument comprises a support connected with the guide such that the guide is movable relative to the support. In some embodiments, the guide translates relative to the support in a lateral and/or transverse orientation relative to the surgical instrument. In some embodiments, the support is selectively adjustable relative to the surgical instrument. In some embodiments, the surgical instrument includes a lock that fixes position of the support relative to the surgical instrument. In some embodiments, the guide position is selectively adjustable relative to the support. In some embodiments, the support and/or guide comprise a T-shape configuration. In some embodiments, the guide includes a first slide for alignment with a lateral portion of a vertebra and a second slide for alignment with a contra-lateral portion of the vertebra. In some embodiments, the first slide is translatable relative to the second slide. In some embodiments, the first slide and/or the second slide include a block that defines a cavity for disposal of a surgical tool such that the block orients the surgical tool along a selected path for penetrating tissue.

In some embodiments, the surgical system comprises a surgical instrument that can be employed with osteotomies for treating advanced spinal deformity applications, such as, primary and revision cases to restore a patient's alignment. In some embodiments, the surgical system comprises a surgical instrument that can be employed with a method comprising an osteotomy, which includes the step of removing a wedge of bone out of a single vertebra. In some embodiments, the method includes the step of closing the wedge and locking the vertebra into place with bone screws for healing. In some embodiments, the method includes the step of selecting an angle for cutting the vertebra to remove the wedge of bone tissue. This configuration of the surgical instrument provides the surgeon with the ability to accurately cut the vertebra and have a point of reference to perform cuts for an osteotomy. In some embodiments, the method includes the step of removing a spinous process of one or more selected vertebra. In some embodiments, the method includes the step of performing a laminectomy of one or more selected vertebra.

In some embodiments, the surgical instrument includes a base, such as, for example, paddles that rest on an inferior endplate of a superior vertebra. In some embodiments, the paddles are held in place by a connector, such as, for example, a rod that fits into a bone screw head to maintain location and increase stability of the surgical instrument for a procedure, as described herein. In some embodiments, the base includes a lip such that a portion of the base can be positioned within an intervertebral space.

In some embodiments, the surgical instrument includes one or more rods connected with bone fastener(s). In some embodiments, the rods stabilize the surgical instrument against a superior endplate of an inferior vertebra. In some embodiments, the rods and/or the surgical instrument are positionally adjustable to facilitate connection of the rods with bone fasteners, for example, multi-axial screws. In some embodiments, the rods and/or the surgical instrument can include a lock to fix position of the rods and/or the surgical instrument relative to the bone fasteners and/or one or more vertebra.

In some embodiments, the paddles are connected to the support, which is relatively perpendicular to the paddles and includes the guide that orients a surgical tool for an upward angle cut. In some embodiments, the support is disposed at a fixed angle relative to the paddles and includes the guide that is movable and/or adjustable to change the angle intersection point relative to one or more vertebra. In some embodiments, the guide can be disposed at one or a plurality of angle orientations and/or the guide can be selectively adjustable to a selected angle relative to the paddles and/or one or more vertebra. In some embodiments, the guide can be disposed at angular orientations, such as, for example, 20, 25 and 30 degrees.

In some embodiments, the surgical instrument includes paddles having a surface that defines a cutout or cavity configured for disposal of vertebra such that a distal end of the paddles can be positioned in an intervertebral space.

In some embodiments, the system of the present disclosure may be employed to treat spinal disorders, such as, for example, degenerative disc disease, disc herniation, osteoporosis, spondylolisthesis, stenosis, scoliosis and other curvature abnormalities, kyphosis, tumor and fractures. In some embodiments, the system of the present disclosure may be employed with other osteal and bone related applications, including those associated with diagnostics and therapeutics. In some embodiments, the disclosed system may be alternatively employed in a surgical treatment with a patient in a prone or supine position, and/or employ various surgical approaches to the spine, including anterior, posterior, posterior mid-line, direct lateral, postero-lateral, and/or anterolateral approaches, and in other body regions. The system of the present disclosure may also be alternatively employed with procedures for treating the lumbar, cervical, thoracic, sacral and pelvic regions of a spinal column. The system of the present disclosure may also be used on animals, bone models and other non-living substrates, such as, for example, in training, testing and demonstration.

The system of the present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. Also, in some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, micro-discectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following discussion includes a description of a surgical system including a surgical instrument, related components and methods of employing the surgical system in accordance with the principles of the present disclosure. Alternate embodiments are also disclosed. Reference is made in detail to the exemplary embodiments of the present disclosure, which are illustrated in the accompanying figures. Turning to FIGS. 1 and 2, there are illustrated components of a surgical system 10.

The components of system 10 can be fabricated from biologically acceptable materials suitable for medical applications, including metals, synthetic polymers, ceramics and/or their composites. For example, the components of system 10, individually or collectively, can be fabricated from materials such as stainless steel alloys, aluminum, commercially pure titanium, titanium alloys, Grade 5 titanium, super-elastic titanium alloys, cobalt-chrome alloys, stainless steel alloys, superelastic metallic alloys (e.g., Nitinol, super elasto-plastic metals, such as GUM METAL® manufactured by Toyota Material Incorporated of Japan), ceramics and composites thereof, thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, and their combinations. Various components of system 10 may have material composites, including the above materials, to achieve various desired characteristics such as strength, rigidity, elasticity, compliance, biomechanical performance, durability and radiolucency or imaging preference. The components of system 10, individually or collectively, may also be fabricated from a heterogeneous material such as a combination of two or more of the above-described materials. The components of system 10 may be monolithically formed, integrally connected or include fastening elements and/or instruments, as described herein.

System 10 includes a surgical instrument 12 that is employed to orient a surgical tool (not shown), such as, for example, a chisel, a drill and/or an osteotome along one or more selected paths for penetrating tissue, as described herein. Instrument 12 includes a member, such as, for example, a support 14. Support 14 is configured for placement and alignment of a base, such as, for example, paddles 30, as described herein.

Support 14 includes a frame 18 extending between an end 20 and an end 22. Frame 18 includes a surface 24 that is connected with paddles 30. In some embodiments, surface 24 defines at least one cavity configured for disposal of paddle 30. In one embodiment, paddles 30 can be monolithically formed with frame 18. In one embodiment, surface 24 may have alternate surface configurations, such as, for example, rough, arcuate, undulating, mesh, porous, semi-porous, dimpled and/or textured. In some embodiments, frame 18 is adjustable, such as, for example, by employing of a nail, key, keyway, nub, friction fit, detent, post and/or releasable lock.

Support 14 includes paddles 30, which are moveable relative to frame 18 for placement and alignment with tissue, such as, for example, an intervertebral space, as described herein. Each paddle 30 extends between an end 32 and an end 34. Each paddle 30 includes a surface 36 and a surface 38. Each paddle 30 defines a longitudinal axis. In some embodiments, the axes of paddles 30 define a transverse plane of vertebrae.

Surfaces 36, 38 are configured for engagement with a vertebral endplate to stabilize support 14 and/or surgical instrument 12 with tissue, such as, for example, vertebrae. Surface 38 includes an axial face, such as, for example, a lip 40 and a transverse face 42 that define a cutout 44 configured to engage and contact tissue adjacent an intervertebral space, such as, for example, vertebrae, endplate tissue, intervertebral tissue, dura matter, spinal cord tissue and/or other vertebral tissue to stabilize support 14 and/or surgical instrument 12 with tissue, such as, for example, vertebrae.

Cutout 44 is configured to facilitate alignment of paddles 30 at a zero degree angle relative to an endplate, such as, for example, an inferior endplate of a superior vertebrae such that cutout 44 is disposed in a square and fixed engagement with endplate surfaces. In some embodiments, all or only a portion of paddles 30 may have various cross-section configurations, such as, for example, arcuate, cylindrical, oblong, rectangular, polygonal, undulating, irregular, uniform, non-uniform, consistent, variable, and/or U-shape.

Support 14 includes a lateral rod 50 extending therefrom. Rod 50 is configured for connection with a bone screw 120 attached with a lateral portion of vertebrae. Support 14 includes a contra-lateral rod 52 extending therefrom. Rod 52 is configured for connection with a bone screw 120 attached with a contra-lateral portion of vertebrae. In some embodiments, bone screws 120 may be attached with tissue, bone and/or vertebrae in various orientations, such as, for example, those alternatives described herein.

Rods 50, 52 each have a cylindrical cross section configuration. In some embodiments, rods 50, 52 can have a uniform thickness/diameter. In some embodiments, rods 50, 52 may have various surface configurations, such as, for example, rough, threaded for connection with surgical instruments, arcuate, undulating, dimpled, polished and/or textured. In some embodiments, the thickness defined by rods 50, 52 may be uniformly increasing or decreasing, or have alternate diameter dimensions along its length. In some embodiments, rods 50, 52 may have various cross section configurations, such as, for example, oval, oblong, triangular, rectangular, square, polygonal, irregular, uniform, non-uniform, variable and/or tapered. In some embodiments, rods 50, 52 may have various lengths.

Support 14 includes a receiver 60 that comprises a cavity for disposal of an arm, such as, for example, an adjustable slide 70, as described herein, for facilitating adjustment, relative movement and/or locking of the components of surgical instrument 12, as described herein. Receiver 60 includes a lock, which comprises a thread form configured for engagement with a coupling member, such as, for example, a set screw (not shown). The set screw is threaded with receiver 60 to attach, provisionally fix and/or lock slide 70 with frame 18.

Slide 70 is configured for connection with frame 18 via receiver 60. Slide 70 is axially translatable relative to frame 18 to position a member, such as, for example, a guide relative to surgical instrument 12 and/or vertebral tissue, as described herein. Slide 70 extends between an end 72 and an end 74. End 72 is configured for disposal with receiver 60. In some embodiments, slide 70 has a T shaped configuration.

End 74 includes a surface 76 that defines cavities 78. Cavities 78 are configured for disposal of guide, which includes an angle block 90 configured for alignment with a lateral portion of vertebrae and an angle block 91 configured for alignment with a contra-lateral portion of vertebrae. In some embodiments, blocks 90, 91 may be aligned with tissue, bone and/or vertebrae in various orientations, such as, for example, those alternatives described herein. Slide 70 extends laterally in a first direction to support block 90 and laterally in a second direction to support block 91, as shown in FIG. 1. The lateral extensions of slide 70 are uniformly configured such that blocks 90, 91 are similarly oriented relative to tissue, as described herein. In some embodiments, the extensions of slide 70 may each extend in alternate orientations, such as, for example, perpendicular, transverse, parallel, offset, staggered and/or at angular orientations.

Slide 70 is axially translatable relative to frame 18 for adjustment of slide 70 relative to one or more components of support 14, for example, along a sagittal plane of vertebrae. Slide 70 includes an outer surface 80 configured for engagement with receiver 60 such that engagement of the set screw with receiver 60 causes the set screw to engage slide 70 and the surfaces of frame 18 to lock frame 18 and slide 70 in a selected orientation.

Block 90 includes a surface 102 that defines an opening 104. Opening 104 is disposed at a selected angular orientation α relative to axis X of lateral paddle 30 disposed, for example, adjacent a lateral portion of vertebrae. As such, opening 104 is configured for disposal of a surgical tool, as described herein, and orienting the surgical tool at angle α relative to axis X. Block 91 includes a surface 106 that defines an opening 110. Opening 110 is disposed at a selected angular orientation α1 relative to an axis X1 of contra-lateral paddle 30 disposed, for example, adjacent a contra-lateral portion of vertebrae. As such, opening 110 is configured for disposal of a surgical tool, as described herein, and orienting the surgical tool at angle α1 relative to axis X1.

In some embodiments, blocks 90, 91 can be pre-configured such that opening 104 and/or opening 110 are disposed at a selected angle. In some embodiments, system 10 comprises a kit that includes one or a plurality of blocks having alternately angled openings. In some embodiments, blocks 90, 91 can be adjusted, for example, with slide 70 for disposal of opening 104 and/or opening 110 at a selected angle.

Openings 104, 110 are disposed at angles α, α1 relative to axes X, X1 of paddles 30 to selectively guide one or more surgical tools along one or more pathways P for penetrating tissue of vertebrae, as described herein. Blocks 90, 91 extend in a similar configuration from slide 70 such that openings 104, 110 are disposed at angles α, α1 and angles α, α1 are substantially equal. In one embodiment, angle α and/or angle α1 is approximately 20 degrees. In one embodiment, angle α and/or angle α1 is approximately 25 degrees. In one embodiment, angle α and/or angle α1 is approximately 30 degrees. In some embodiments, angle α and/or angle α1 may include an angle in a range of angular measurements in a range of 0 through 180 degrees. In some embodiments, angle α and/or angle α1 may be different.

Figure 4:
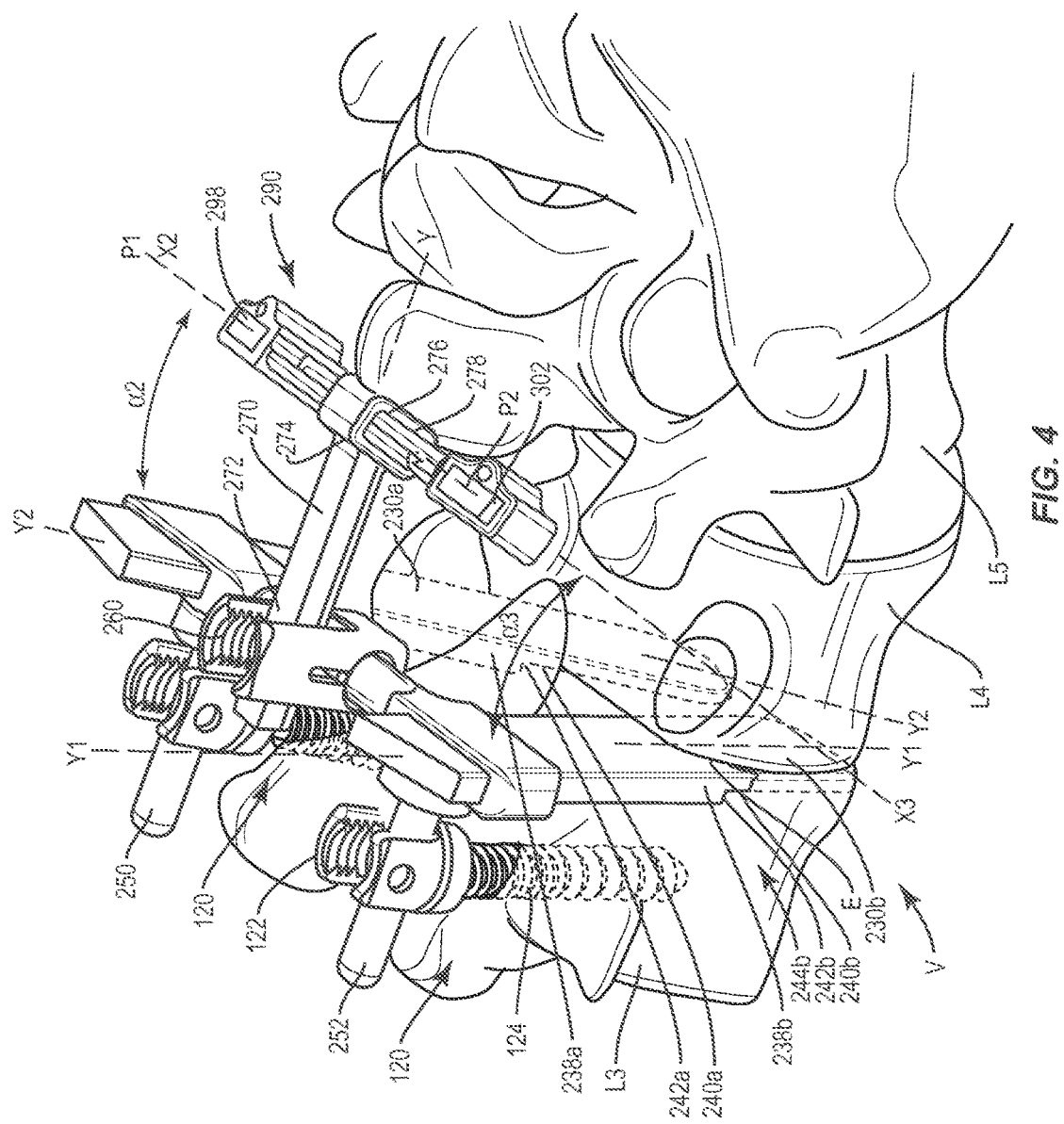
FIG. 4 is a perspective view of the components of the system shown in FIG. 3 disposed with vertebrae.

Each of bone screws 120, as shown in FIG. 4, include a receiver 122 and an elongated shaft 124 configured for penetrating tissue. Receiver 122 includes a pair of spaced apart arms having an inner surface that defines a U-shaped passageway configured for disposal of rods 50, 52. In one embodiment, each of bone screws 120 have a multi axial configuration such that receiver 122 is rotatable to a selected angle through and within an angular range to capture rod 50 and/or rod 52 for fixation therein. The inner surface of receiver 122 includes a thread form configured for engagement with a coupling member, such as, for example, a set screw. The set screw is threaded with the receiver to attach, provisionally fix and/or lock rod 50 and/or rod 52 with at least one of bone screws 120. In some embodiments, other engaging structures may be located on shaft 124, such as, for example, a nail configuration, barbs, expanding elements, raised elements and/or spikes to facilitate engagement of the shaft with tissue, such as, for example, vertebrae.

In assembly, operation and use, system 10, similar to the systems and methods described herein, is employed with a surgical procedure, such as, for example, a correction treatment to treat trauma of the spine, such as, for example, thoraco-lumbar and lumbar fractures. In some embodiments, system 10 can be employed with osteotomies for treating advanced spinal deformity applications, such as, primary and revision cases to restore a patient's alignment. In some embodiments, one or all of the components of system 10 can be delivered or utilized as a pre-assembled device or can be assembled in situ.

For example, system 10 can be employed with a surgical correction treatment of an applicable condition or injury of an affected section of a spinal column and adjacent areas within a body, such as, for example, vertebral levels L1-L5. In some embodiments, system 10 may be employed with one or a plurality of vertebrae.

In use, to treat vertebral levels L1-L5, a medical practitioner obtains access to a surgical site including vertebral levels L1-L5 in any appropriate manner, such as through incision and retraction of tissues. In some embodiments, system 10 can be used in any existing surgical method or technique including open surgery, mini-open surgery, minimally invasive surgery and percutaneous surgical implantation, whereby vertebral levels L1-L5 are accessed through a mini-incision, or sleeve that provides a protected passageway to the area. Once access to the surgical site is obtained, the particular surgical procedure can be performed for treating a spine disorder.

An incision is made in the body of a patient and a cutting instrument (not shown) creates a surgical pathway for implantation of components of system 10. A preparation instrument (not shown) can be employed to prepare tissue surfaces of vertebral levels L1-L5 as well as for aspiration and irrigation of a surgical region.

Pilot holes are made in vertebral level L3 of vertebrae V for receiving one or more bone screws 120. Shaft 124 of each bone screw 120 is oriented with the bony anatomy of vertebral level L3 and a driver (not shown) is manipulable to drive, torque, insert or otherwise fasten each bone screw 120 with vertebral level L3. Each shaft 124 is threaded and engaged with tissue.

In some embodiments, surgical instrument 12 is employed with a PSO procedure. Vertebral level L4 is identified for treatment such that all or a portion of the vertebra is cut and/or removed in connection with the PSO procedure. One or more pathways, such as, for example, selected path P, as shown in FIG. 2, which corresponds to angles α, α1 of blocks 90, 91 for cutting vertebra L4 is determined. In some embodiments, angle α and/or angle α1 angle is measured and/or determined within a sagittal plane of vertebrae V from an inferior endplate E of a superior vertebra L3 relative to vertebra L4.

Surgical instrument 12 is employed to orient a surgical tool (not shown), such as, for example, a chisel, drill and/or osteotome along selected path P for penetrating tissue. The chisel, drill and/or osteotome cuts and/or removes all or a portion of vertebra L4. In some embodiments, the chisel, drill and/or osteotome cuts and/or removes a wedge of vertebra L4. This configuration of surgical instrument 12 provides the surgeon with the ability to accurately cut vertebra L4 and have a point of reference to perform cuts for an osteotomy. In some embodiments, the PSO includes removing a spinous process of selected vertebrae, such as, for example, vertebra L3 and/or vertebra L4. In some embodiments, the PSO includes performing a laminectomy of selected vertebrae, such as, for example, vertebra L3 and/or vertebra L4.

Support 14 is aligned over vertebrae V such that rod 50 is disposed with bone screw 120 along a lateral portion of vertebrae V. Rod 52 is disposed with bone screw 120 along a contra-lateral portion of vertebrae V. Receivers 122 can be manipulated to facilitate positioning of support 14 relative to vertebrae V. Paddles 30 are manipulated relative to frame 18, in the direction shown by arrows A and B in FIG. 2, for placement and alignment of paddle 30 with an intervertebral space between vertebrae L3, L4. Paddles 30 are aligned with vertebrae L3, L4 such that axes X, X1 are oriented at a zero degree angle relative to inferior endplate E of superior vertebra L3. Cutout 44 of paddle 30 is disposed in a square and fixed engagement with endplate surface E. This configuration provides stability for mounting of the components of surgical instrument 12 with paddle 30 and vertebrae L3, L4 for accurately penetrating and/or cutting tissue with the surgical tool.

Blocks 90, 91 are disposed with slide 70, as described herein. Slide 70 is positioned within receiver 60 and axially translated, in the direction shown by arrows C and D in FIG. 1, for orientation of blocks 90, 91 with vertebrae V. In some embodiments, blocks 90, 91 may be selected from a system or kit such that openings 104, 110 are disposed at selected angles α, α1 along path P. In some embodiments, blocks 90, 91 may be fixed with slide 70 and/or adjustable with slide 70 such that openings 104, 110 are disposed at selected angles α, α1 along path P. The set screw is engaged with receiver 60 to fix slide 70 with frame 18 and lock paddles 30 in a fixed orientation relative to vertebrae V.

Upon adjustment and selective positioning of the components of surgical instrument 12, which may include selection of block 90 and/or block 91 including an opening being disposed at a selected angle α long path P, as described herein, and/or adjustment of blocks 90, 91 in transverse and/or sagittal planes of vertebrae V, as described herein, openings 104, 110 are disposed at angles α, α1 along path P. Openings 104, 114, measured and/or determined from inferior endplate E relative to the vertebra L4, orient the surgical tool along path P to cut and/or remove all or a portion of vertebra L4.

The surgical tool is introduced through openings 104, 114 along path P and translated into engagement with vertebra L4. The surgical tool is oriented to cut a portion of vertebra L4 along path P at angles α, α1 to remove a bone and/or tissue wedge from vertebral level L4. In some embodiments, the PSO includes closing the space corresponding to the removed or wedge portion of vertebra L4 and locking vertebra L4 into place with bone screws for healing. In some embodiments, surgical instruments may be employed in connection with the PSO to manipulate bone screws 120 and/or introduce a spinal rod (not shown) into receivers 122. In some embodiments, surgical instruments may be employed in connection with the PSO so that vertebrae connected with bone screws can be compressed and/or distracted. In some embodiments, surgical instruments may be employed in connection with the PSO to compress and/or distract vertebrae connected with bone screws to restore vertebral body height and curvature of vertebrae by rotating vertebrae about a center of rotation corresponding to a bone screw adjacent a facet joint.

Upon completion of a procedure, as described herein, the surgical instruments, assemblies and non-implanted components of system 10 are removed and the incision(s) are closed. One or more of the components of system 10 can be made of radiolucent materials such as polymers. Radiomarkers may be included for identification under x-ray, fluoroscopy, CT or other imaging techniques. In some embodiments, the use of surgical navigation, microsurgical and image guided technologies may be employed to access, view and repair spinal deterioration or damage, with the aid of system 10. In some embodiments, system 10 may include one or a plurality of rods, plates, connectors and/or bone fasteners for use with a single vertebral level or a plurality of vertebral levels.

In some embodiments, one or more of fasteners 120 may be engaged with tissue in various orientations, such as, for example, series, parallel, offset, staggered and/or alternate vertebral levels. In some embodiments, one or more of fasteners 120 may comprise multi-axial screws, sagittal angulation screws, pedicle screws, mono-axial screws, uniplanar screws, facet screws, fixed axis screws, tissue penetrating screws, conventional screws, expanding screws, wedges, anchors, buttons, clips, snaps, friction fittings, compressive fittings, expanding rivets, staples, nails, adhesives, posts, fixation plates and/or posts.

In one embodiment, system 10 includes an agent, which may be disposed, packed, coated or layered within, on or about the components and/or surfaces of system 10. In some embodiments, the agent may include bone growth promoting material, such as, for example, bone graft to enhance fixation of the components and/or surfaces of system 10 with vertebrae. In some embodiments, the agent may include one or a plurality of therapeutic agents and/or pharmacological agents for release, including sustained release, to treat, for example, pain, inflammation and degeneration.

In one embodiment, as shown in FIGS. 3 and 4, system 10, similar to the systems and methods described with regard to FIGS. 1 and 2, includes instrument 212, similar to instrument 12 described above. Instrument 212 includes a support 214, similar to support 14 described herein. Support 214 is configured for placement and alignment of paddles 230a, 230b, similar to paddles 30 described herein.

Support 214 includes a frame 218. Frame 218 includes a part 218a and a part 218b configured for slidable engagement such that part 218a and part 218b are disposed in a telescoping configuration. Part 218a is translatable relative to part 218b. Part 218a includes a collar 220 having an inner surface that defines a cavity 222. Collar 220 is connected with part 218a via a spherical joint, such as, for example, a ball and socket to facilitate relative movement of the components. Cavity 222 is configured for moveable disposal of paddle 230a such that paddle 230a translates relative to frame 218. Part 218b includes a collar 224 having an inner surface that defines a cavity 226. Collar 224 is connected with part 218b via a spherical joint, such as, for example, a ball and socket to facilitate relative movement of the components. Cavity 226 is configured for moveable disposal of paddle 230b such that paddle 230b translates relative to frame 218.

Translation of parts 218a, 218b and rotation of collars 220, 224 relative to frame 218 facilitates orientation of cavities 222, 226 with paddles 230a, 230b relative to vertebrae for placement and alignment with an intervertebral space, as described herein. Paddle 230a defines a longitudinal axis Y2 and paddle 230b defines a longitudinal axis Y1.

Paddle 230a extends between end 232a and end 234a. Paddle 230b extends between end 232b and end 234b. Paddle 230a includes surfaces 236a, 238a, and paddle 230b includes surfaces 236b, 238b. Surfaces 236a, 236b, 238a, 238b are configured for engagement with tissue of vertebral endplates to stabilize support 214 and/or surgical instrument 212 with vertebrae.

Surface 238a includes an axial face, such as, for example, a lip 242a and a transverse face 240a that define a cutout 244a configured to engage and contact tissue adjacent an intervertebral space, such as, for example, vertebrae, endplate tissue, intervertebral tissue, dura matter, spinal cord tissue and/or other vertebral tissue to stabilize support 214 and/or surgical instrument 212 with tissue, such as, for example, vertebrae.

Cutout 244a is configured to facilitate alignment of paddle 230a at a zero degree angle relative to an endplate, such as, for example, an inferior endplate of a superior vertebra such that cutout 244a is disposed in a square and fixed engagement with endplate surfaces. In some embodiments, all or only a portion of paddle 230a may have various cross-section configurations, such as, for example, arcuate, cylindrical, oblong, rectangular, polygonal, undulating, irregular, uniform, non-uniform, consistent, variable, and/or U-shape.

Surface 238b includes an axial face, such as, for example, a lip 242b and a transverse face 240b that define a cutout 244b configured to engage and contact tissue adjacent an intervertebral space, such as, for example, vertebrae, endplate tissue, intervertebral tissue, dura matter, spinal cord tissue and/or other vertebral tissue to stabilize support 214 and/or surgical instrument 212 with tissue, such as, for example, vertebrae.

Cutout 244b is configured to facilitate alignment of paddle 230b at a zero degree angle relative to an endplate, such as, for example, an inferior endplate of a superior vertebra such that cutout 244b is disposed in a square and fixed engagement with endplate surfaces. In some embodiments, all or only a portion of paddle 230b may have various cross-section configurations, such as, for example, arcuate, cylindrical, oblong, rectangular, polygonal, undulating, irregular, uniform, non-uniform, consistent, variable, and/or U-shape.

Support 214 includes a lateral rod 250, similar to rod 50 and/or rod 52 described herein, extending therefrom. Rod 250 is configured for connection with a bone screw 120, as described herein, which is attached with a lateral portion of vertebrae, such as, for example, vertebra L4. Support 214 includes a contra-lateral rod 252, similar to rod 50 and/or rod 52, extending therefrom. Rod 52 is configured for connection with a bone screw 120 attached with a contra-lateral portion of vertebrae.

Support 214 includes a lock, such as, for example, a receiver 260 that comprises a cavity for disposal of an arm, such as, for example, an adjustable slide 270, similar to slide 70 described herein, that facilitates adjustment, relative movement and/or locking of the components of surgical instrument 212, as described herein. Receiver 260 includes a pair of spaced apart arms 262 having an inner surface 264 that defines a U-shaped passageway 266 configured for moveable disposal of slide 270. Inner surface 264 includes a thread form configured for engagement with a coupling member, such as, for example, a set screw (not shown). The set screw is threaded with receiver 260 to attach, provisionally fix and/or lock slide 270 with frame 218.

Slide 270 is configured for connection with frame 218 via receiver 260. Slide 270 defines an axis Y. Slide 270 is axially translatable relative to frame 218 to position a member, such as, for example, a guide relative to surgical instrument 212 and/or vertebral tissue, as described herein. Slide 270 is axially translatable relative to frame 218 to position a guide 290 relative to paddles 230a, 230b, as described herein.

Slide 270 extends between an end 272 and an end 274. End 272 is configured for disposal with receiver 260. End 274 includes an inner surface 276 that defines a cavity 278. Cavity 278 is configured for disposal of the components of guide 290. The components of guide 290 are supported within cavity 278 by surface 276 to dispose the components of guide 290 at a selected angular orientation relative to axes Y1, Y2 of paddles 230a, 230b for orienting a surgical tool to penetrate tissue, as described herein.

In some embodiments, slide 270 can be pre-configured such that the components of guide 290 are disposed at a selected angle. In some embodiments, system 10 comprises a kit that includes one or a plurality of slides to dispose the guides at alternate angles. In one embodiment, slide 270 orients the components of guide 290 at an angle of approximately 20 degrees. In one embodiment, slide 270 orients the components of guide 290 at an angle of approximately 25 degrees. In one embodiment, slide 270 orients the components of guide 290 at an angle of approximately 30 degrees. In some embodiments, slide 270 orients the components of guide 290 at an angle in a range of 0 through 180 degrees.

Slide 270 includes an outer surface 280 configured for engagement with arms 262 and surface 264 such that engagement of the set screw with receiver 260 causes the set screw to engage surface 280 such that arm 270 applies an axial force to frame 218 to lock frame 218 and paddles 230a, 230b in a selected orientation.

Guide 290 includes a slide 292 and a slide 294. Slides 292, 294 are configured for slidable engagement such that slide 292 is translatable relative to slide 294. Slides 292, 294 are connected via a pin and slot engagement. Slide 292 includes an inner surface 296 that defines a cavity 298. Slide 294 includes an inner surface 300 that defines a cavity 302.

Cavity 298 is configured for disposal of a surgical tool and alignment with a lateral portion of vertebrae, such as, for example, vertebra L4 and cavity 302 is configured for disposal of a surgical tool and alignment with a contra-lateral portion of vertebra L4. In some embodiments, cavities 298, 302 may be aligned with tissue, bone and/or vertebrae in various orientations, such as, for example, those alternatives described herein. Slide 292 extends laterally in a first direction from slide 270 to support a surgical tool and slide 294 extends laterally in a second direction from slide 270 to support a surgical tool. Slides 292, 294 are uniformly configured such that cavities 298, 302 are similarly oriented relative to tissue, as described herein. In some embodiments, slides 292, 294 and/or cavities 298, 302 may each extend in alternate orientations, such as, for example, perpendicular, transverse, parallel, offset, staggered and/or at angular orientations.

Cavity 298 defines an axis X2 and is disposed at a selected angular orientation $\alpha 2$ relative to axis Y2 of lateral paddle 230a disposed, for example, adjacent a lateral portion of vertebrae. As such, cavity 298 is configured for disposal of a surgical tool, as described herein, and orienting the surgical tool at angle $\alpha 2$ relative to axis Y2. Cavity 302 defines an axis X3 and is disposed at a selected angular orientation $\alpha 3$ relative to axis Y1 of contra-lateral paddle 230b disposed, for example, adjacent a contra-lateral portion of vertebrae. As such, cavity 302 is configured for disposal of a surgical tool, as described herein, and orienting the surgical tool at angle $\alpha 3$ relative to axis Y1.

In some embodiments, slides 292, 294 can be pre-configured such that cavity 298 and/or cavity 302 are disposed at a selected angle. In some embodiments, system 10 comprises a kit that includes one or a plurality of slides having alternately angled cavities. In some embodiments, slides 292, 294 can be adjusted, for example, to dispose cavity 298 and/or cavity 302 at a selected angle.

Cavities 298, 302 are disposed at angles $\alpha 2$, $\alpha 3$ relative to axes Y2, Y1 of paddles 230a, 230b to selectively guide a surgical tool along pathways P1, P2, respectively, for penetrating tissue of vertebrae, as described herein. Slides 292, 294 extend in a similar configuration from slide 270 such that cavities 298, 302 are disposed at angles $\alpha 2$, $\alpha 3$ and angles $\alpha 2$, $\alpha 3$ are substantially equal. In one embodiment, angle α2 and/or angle α3 is approximately 20 degrees. In one embodiment, angle α2 and/or angle α3 is approximately 25 degrees. In one embodiment, angle α2 and/or angle α3 is approximately 30 degrees. In some embodiments, angle α2 and/or angle α3 may include an angle in a range of angular measurements in a range of 0 through 180 degrees. In some embodiments, angle α2 and/or angle α3 may be different.

In assembly, operation and use, system 10 including surgical instrument 212, similar to the systems and methods described herein, is employed with a surgical procedure. Pilot holes are made in vertebral level L3 of vertebrae V for receiving one or more bone screws 120. Shaft 124 of each bone screw 120 is oriented with the bony anatomy of vertebral level L3 and a driver (not shown) is manipulable to drive, torque, insert or otherwise fasten each bone screw 120 with vertebral level L3. Each shaft 124 is threaded and engaged with tissue.

Surgical instrument 212 is employed with a PSO procedure. Vertebral level L4 is identified for treatment such that all or a portion of the vertebra is cut and/or removed in connection with the PSO procedure. Selected paths P1, P2, as shown in FIG. 4, which correspond to angles α2, α3 of slides 292, 294, as described herein, for cutting vertebra L4 is determined.

Surgical instrument 212 is employed to orient one or more surgical tools (not shown), such as, for example, a chisel, drill and/or osteotome along selected paths P1, P2 for penetrating tissue. The chisel, drill and/or osteotome cuts and/or removes all or a portion of vertebra L4. In some embodiments, the chisel, drill and/or osteotome cuts and/or removes a wedge of vertebra L4. This configuration of surgical instrument 212 provides the surgeon with the ability to accurately cut vertebra L4 and have a point of reference to perform cuts for an osteotomy.

Support 214 is aligned over vertebrae V such that rod 250 is disposed with bone screw 120 along a lateral portion of vertebrae V. Rod 252 is disposed with bone screw 120 along a contra-lateral portion of vertebrae V. Receivers 122 can be manipulated to facilitate positioning of support 214 relative to vertebrae V. Paddles 230a, 230b are manipulated relative to frame 218 for placement and alignment of paddles 230a, 230b with an intervertebral space between vertebrae L3, L4. Paddles 230a, 230b are aligned with vertebrae L3, L4 such that axes Y2, Y1 are oriented at a zero degree angle relative to an inferior endplate of superior vertebra L3. Cutouts 244a, 244b are disposed in a square and fixed engagement with the endplate surfaces. This configuration provides stability for mounting of the components of surgical instrument 212 with paddles 230a, 230b and vertebrae L3, L4 for accurately penetrating and/or cutting tissue with the surgical tools.

Slides 292, 294 are disposed with slide 270, as described herein. Slide 270 is positioned within receiver 260 and axially translated for orientation of slides 292, 294 with vertebrae V. The set screw is engaged with receiver 260 to fix slide 270 with frame 218 and lock paddles 230a, 230b in a fixed orientation relative to vertebrae V.

Upon adjustment and selective positioning of the components of surgical instrument 212, as described herein, cavities 298, 302 are disposed at angles α2, α3 along paths P1, P2. Cavities 298, 302, measured and/or determined from the inferior endplate relative to vertebra L4, orient the surgical tools along paths P1, P2 to cut and/or remove all or a portion of vertebra L4.

The surgical tools are introduced through cavities 298, 302 along paths P1, P2 and translated into engagement with vertebra L4. The surgical tools are oriented to cut a portion of vertebra L4 along paths P1, P2 at angles α2, α3 to remove a bone and/or tissue wedge from vertebral level L4. Upon completion of a procedure, as described herein, the surgical instruments, assemblies and non-implanted components of system 10 are removed and the incision(s) are closed.

Figure 5:
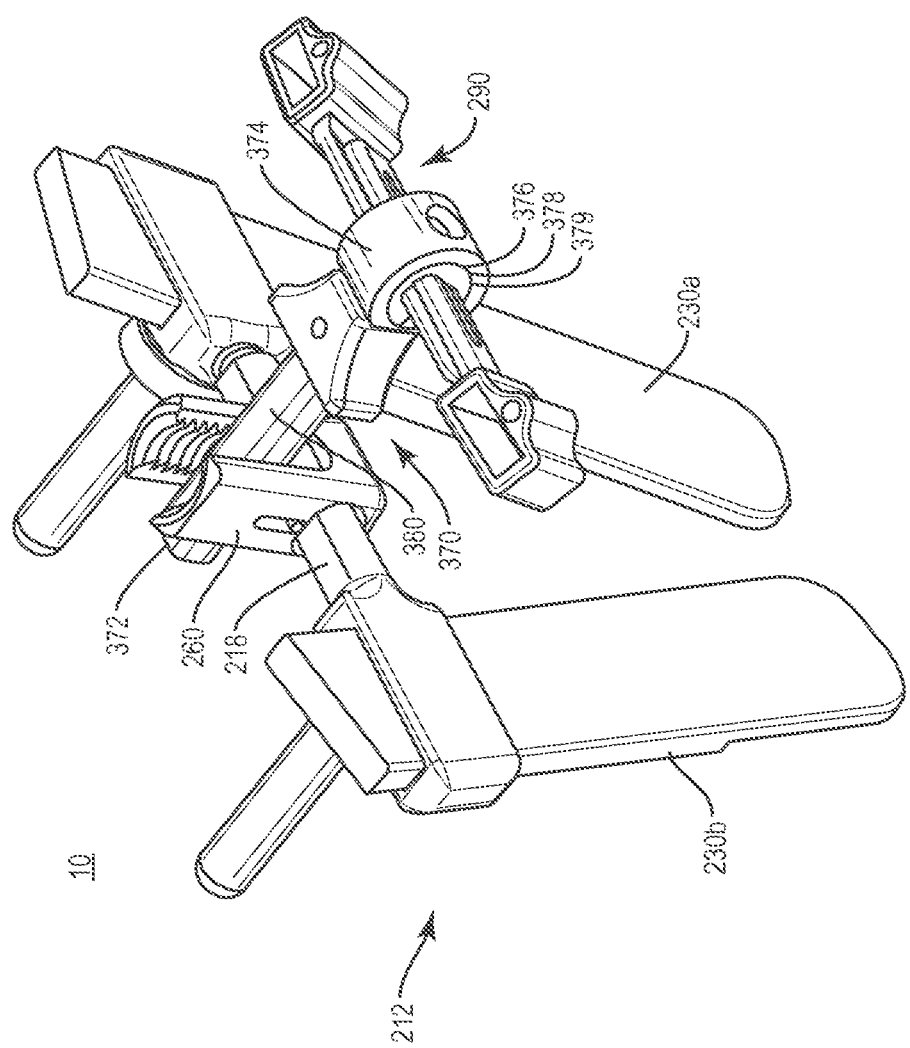
FIG. 5 is a perspective view of components of one embodiment of a system in accordance with the principles of the present disclosure.

In one embodiment, as shown in FIG. 5, system 10 including surgical instrument 212, similar to the systems and methods described with regard to FIGS. 3 and 4, has an adjustable slide 370, similar to slide 270 described herein. Receiver 260 is configured for disposal of slide 370 for facilitating adjustment, relative movement and/or locking of the components of surgical instrument 212, as described herein.

Slide 370 is configured for connection with frame 218 via receiver 260. Slide 370 is axially translatable relative to frame 218 to position a member, such as, for example, guide 290 relative to surgical instrument 212 and/or vertebral tissue, as described herein. Slide 370 is axially translatable relative to frame 218 to position slides 292, 294 of guide 290 relative to paddles 230a, 230b, as described herein.

Slide 370 extends between an end 372 and an end 374. End 372 is configured for disposal with receiver 260. End 374 includes an inner surface 376 that defines a cavity 378. Cavity 378 is configured for disposal of an insert 379. Insert 379 is rotatable within and relative to surface 376. Insert 379 supports the components of guide 290 and rotates slides 292, 294 relative to the components of surgical instrument 212 and vertebrae. Slides 292, 294 are supported within cavity 378 by surface 276 to selectively adjust and rotate cavities 298, 302 of slides 292, 294 to a selected angular orientation relative to axes Y1, Y2 (FIGS. 3 and 4) of paddles 230a, 230b for orienting one or more surgical tools to penetrate tissue, as described herein. In some embodiments, the components of guide 290 can be rotated relative to the components of surgical instrument 212 and vertebrae through an angular range of 0 through 360 degrees.

Slide 370 includes an outer surface 380 configured for engagement with arms 262 and surface 264 such that engagement of the set screw with receiver 260 causes the set screw to engage surface 380 such that slide 370 applies an axial force to frame 218 to lock frame 218 and paddles 230a, 230b in a selected orientation, as described herein.

Figure 6:
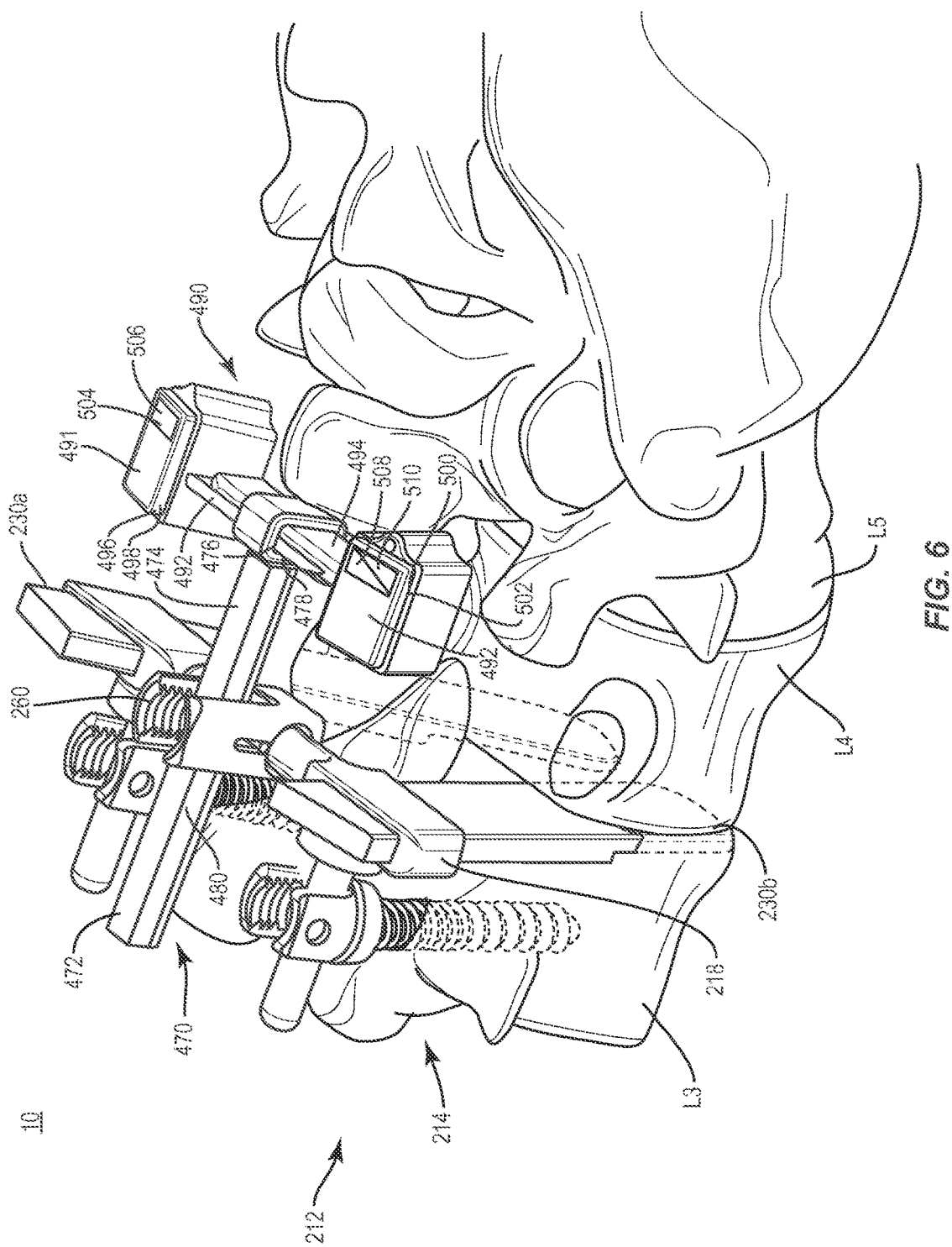
FIG. 6 is a perspective view of components of one embodiment of a system in accordance with the principles of the present disclosure disposed with vertebrae.

In one embodiment, as shown in FIG. 6, system 10 including surgical instrument 212, similar to the systems and methods described with regard to FIGS. 3 and 4, has an adjustable slide 470, similar to slide 270 described herein. Receiver 260 is configured for disposal of slide 470 to facilitate adjustment, relative movement and/or locking of the components of surgical instrument 212, as described herein.

Slide 470 is configured for connection with frame 218 via receiver 260. Slide 470 is axially translatable relative to frame 218 to position a member, such as, for example, a guide 490 relative to surgical instrument 212 and/or vertebrae L3-L5, as described herein. Slide 470 is axially translatable relative to frame 218 to position slides 492, 494 of guide 490 relative to paddles 230a, 230b, as described herein.

Slide 470 extends between an end 472 and an end 474. End 472 is configured for disposal with receiver 260. End 474 includes an inner surface 476 that defines a cavity 478. Cavity 478 is configured for disposal of the components of guide 490. The components of guide 490 are supported within cavity 478 by surface 476 to dispose the components of guide 490 at a selected angular orientation relative to axes Y1, Y2 (FIGS. 3 and 4) of paddles 230a, 230b for orienting a surgical tool to penetrate tissue, as described herein.

Slide 470 is axially translatable relative to frame 218 for adjustment of slide 470 relative to one or more components of support 214, for example, along a sagittal plane of vertebrae. Slide 470 includes an outer surface 480 configured for engagement with arms 262 and surface 264 such that engagement of the set screw with receiver 260 causes the set screw to engage surface 480 such that slide 470 applies an axial force to frame 218 to lock frame 218 and paddles 230a, 230b in a selected orientation.

Slides 492, 494, similar to the slides described herein, are configured for slidable engagement such that slide 492 is translatable relative to slide 494. Slides 492, 494 are connected via a pin and slot engagement. Slide 492 includes an inner surface 496 that defines a cavity 498. Slide 494 includes an inner surface 500 that defines a cavity 502.

Cavity 498 is configured for disposal of an angle block 491 that is configured for alignment with a lateral portion of vertebra L4. Cavity 502 is configured for disposal of an angle block 492 that is configured for alignment with a contra-lateral portion of vertebra L4.

Block 491 includes a surface 504 that defines an opening 506. Opening 506 is disposed at a selected angular orientation, similar to that described herein, relative to axis Y2 of lateral paddle 230a disposed adjacent a lateral portion of vertebra L4. As such, opening 506 is configured for disposal of a surgical tool, as described herein, and orienting the surgical tool at the selected angle relative to axis Y2. Block 492 includes a surface 508 that defines an opening 510. Opening 510 is disposed at a selected angular orientation, similar to that descried herein, relative to axis Y1 of contra-lateral paddle 230b disposed adjacent a contra-lateral portion of vertebra L4. As such, opening 510 is configured for disposal of a surgical tool, as described herein, and orienting the surgical tool at the selected angle relative to axis Y1.

In some embodiments, blocks 491, 492 can be pre-configured such that opening 506 and/or opening 510 are disposed at a selected angle. In some embodiments, system 10 comprises a kit that includes one or a plurality of blocks having alternately angled openings. In some embodiments, blocks 491, 492 can be adjusted, for example, with slide 470 for disposal of opening 506 and/or opening 510 at a selected angle.

Openings 506, 510 are disposed at selected angles relative to axes Y2, Y1 of paddles 230a, 230b to selectively guide one or more surgical tools along one or more pathways, as described herein, for penetrating tissue of vertebra L4, as described herein. Blocks 491, 492 extend in a similar configuration from slide 470 such that openings 506, 510 are disposed at the selected angles, which are substantially equal. In some embodiments, blocks 491, 492 extend such that openings 506, 510 are disposed at alternate and/or different selected angles.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A surgical instrument comprising:
   a first member configured to be connected with tissue, the first member comprising a frame, a first collar coupled to a first end of the frame, a second collar coupled to a second end of the frame, a first paddle positioned within a cavity of the first collar and a second paddle positioned within a cavity of the second collar, the first member including a first rod extending from the first collar and a second rod extending from the second collar, the rods each being connected with a bone fastener that is configured to be attached with tissue; and
   a second member connected with the first member and configured to orient at least one surgical tool along at least one selected path for penetrating tissue.

2. The surgical instrument recited in claim 1, wherein the paddles each include a lip that is configured to engage tissue to stabilize the surgical instrument.

3. The surgical instrument recited in claim 1, wherein the collars are movable relative to the frame.

4. The surgical instrument recited in claim 1, wherein the frame includes a first part and a second part that is disposed in a telescoping configuration with the first part.

5. The surgical instrument recited in claim 1, wherein the frame includes a lock positioned between the collars that includes spaced apart arms that define a cavity therebetween, a slide of the second member being positioned within the cavity of the lock, inner surfaces of the arms comprising a thread form configured to mate with a thread form of a set screw to fix the slide relative to the frame.

6. The surgical instrument recited in claim 1, wherein the second member includes a guide configured for disposal of a surgical tool.

7. The surgical instrument recited in claim 6, wherein the guide includes a first slide and a second slide, the slides being relatively movable.

8. The surgical instrument recited in claim 6, wherein the guide includes at least one angled block.

9. The surgical instrument recited in claim 6, wherein the guide is selectively adjustable to orient the surgical tool at a selected angle relative to the first member.

10. The surgical instrument recited in claim 6, wherein the guide is axially translatable relative to the first member.

11. The surgical instrument recited in claim 1, wherein the collars are each connected with the frame via a ball and socket.

12. A surgical instrument comprising:
    a support configured to be connected with at least one vertebra, the support comprising a frame, a first collar coupled to a first end of the frame, a second collar coupled to an opposite second end of the frame, a first paddle positioned within a cavity of the first collar and a second paddle positioned within a cavity of the second collar, the paddles each being engageable with at least one vertebra to stabilize the surgical instrument, the support including a first rod extending from the first collar and a second rod extending from the second collar, the rods each being connected with a bone fastener that is configured to be attached with tissue;
    an arm positioned within a receiver of the frame; and
    a guide connected with the arm and being configured to orient a surgical tool along at least one selected path for penetrating at least one vertebra.

13. The surgical instrument recited in claim 12, wherein the support is configured to be connected with the at least one vertebra via at least one bone fastener.

14. A surgical instrument comprising:
    a support comprising a frame, a first collar coupled to a first end of the frame, a second collar coupled to a second end of the frame, a first paddle positioned within a cavity of the first collar and a second paddle positioned within a cavity of the second collar, the collars each being connected with the frame via a ball and socket;
    a slide positioned within a receiver of the frame; and a guide connected with the slide and being movable relative to the slide to orient a surgical tool along a selected path, wherein the receiver is positioned between the collars, the receiver including spaced apart arms that define a cavity therebetween, the slide being positioned within the cavity of the receiver, inner surfaces of the arms comprising a thread form configured to mate with a thread form of a set screw to fix the slide relative to the frame.

15. The surgical instrument recited in claim 14, wherein the slide includes a cavity and the guide includes a first part and a second part that is movable relative to the first part, the parts being positioned within the cavity of the slide.

16. The surgical instrument recited in claim 15, wherein the parts are connected via a pin and slot engagement.

17. The surgical instrument recited in claim 15, wherein the first part includes a first passageway and the second part includes a second passageway that is similarly oriented relative to the slide.

18. The surgical instrument recited in claim 15, further comprising an insert positioned within the cavity of the slide such that the insert is rotatable relative to the slide, the parts being positioned within the insert.

* * * * *